US010499682B2

(12) United States Patent
Prasad et al.

(10) Patent No.: US 10,499,682 B2
(45) Date of Patent: Dec. 10, 2019

(54) MICRONUTRIENT FORMULATION IN ELECTRONIC CIGARETTES

(71) Applicants: Kedar Prasad, San Rafael, CA (US); Gerald Haase, Greenwood Village, CO (US)

(72) Inventors: Kedar Prasad, San Rafael, CA (US); Gerald Haase, Greenwood Village, CO (US)

(73) Assignee: New Age Beverage Corporation, Denver, CO (US)

( * ) Notice: Subject to any disclaimer, the term of this patent is extended or adjusted under 35 U.S.C. 154(b) by 612 days.

(21) Appl. No.: 14/756,311

(22) Filed: Aug. 25, 2015

(65) Prior Publication Data

US 2016/0050969 A1    Feb. 25, 2016

Related U.S. Application Data

(60) Provisional application No. 62/070,395, filed on Aug. 25, 2014.

(51) Int. Cl.
| | |
|---|---|
| A24B 15/16 | (2006.01) |
| A24B 15/30 | (2006.01) |
| A61K 31/07 | (2006.01) |
| A61K 31/355 | (2006.01) |
| A61K 31/05 | (2006.01) |
| A61K 36/82 | (2006.01) |
| A61K 31/215 | (2006.01) |
| A61K 9/00 | (2006.01) |
| A24F 47/00 | (2006.01) |

(52) U.S. Cl.
CPC .......... *A24B 15/16* (2013.01); *A24F 47/002* (2013.01); *A61K 9/007* (2013.01); *A61K 9/0053* (2013.01); *A61K 31/05* (2013.01); *A61K 31/215* (2013.01); *A61K 31/355* (2013.01); *A61K 36/82* (2013.01)

(58) Field of Classification Search
CPC .......... A23V 2200/10; A23V 2200/02; A23V 2250/026
See application file for complete search history.

(56) References Cited

U.S. PATENT DOCUMENTS

| | | |
|---|---|---|
| 2,939,821 A | 6/1960 | Eigen et al. |
| 3,446,899 A | 5/1969 | Cavalli et al. |
| 3,584,114 A | 6/1971 | Cavalli |
| 3,777,029 A | 12/1973 | Magid |
| 3,860,733 A | 1/1975 | Morse et al. |
| 4,619,829 A | 10/1986 | Motschan |
| 4,740,373 A | 4/1988 | Kesselman et al. |
| 4,976,960 A | 12/1990 | Grossman et al. |
| 5,084,482 A | 1/1992 | Hirsch et al. |
| 5,223,285 A | 6/1993 | DeMichele et al. |
| 5,292,538 A | 3/1994 | Paul et al. |
| 5,561,160 A | 10/1996 | Walaszek et al. |
| 5,571,441 A | 11/1996 | Andon et al. |
| 5,626,883 A | 5/1997 | Paul |
| 5,629,023 A | 5/1997 | Bland |
| 5,661,123 A | 8/1997 | Stalker et al. |
| 5,788,971 A | 8/1998 | Togasaki |
| 5,895,652 A | 4/1999 | Giampapa |
| 5,922,346 A | 7/1999 | Hersh |
| 5,922,704 A | 7/1999 | Bland |
| 5,939,394 A | 8/1999 | Fleming et al. |
| 5,948,823 A | 9/1999 | Ben-Amotz |
| 5,976,568 A | 11/1999 | Riley |
| 5,985,339 A | 11/1999 | Kamarei |
| 6,048,846 A | 4/2000 | Cochran |
| 6,066,327 A | 5/2000 | Gubernick |
| 6,068,848 A | 5/2000 | Gubernick |
| 6,080,788 A | 6/2000 | Sole et al. |
| 6,090,414 A | 7/2000 | Passwater et al. |
| 6,117,872 A | 9/2000 | Maxwell et al. |
| 6,124,268 A | 9/2000 | Ghosal |
| 6,130,244 A | 10/2000 | DeMichele et al. |
| 6,139,872 A | 10/2000 | Walsh |
| 6,143,301 A | 11/2000 | de la Harpe et al. |
| 6,149,452 A | 11/2000 | Chen et al. |
| 6,162,468 A | 12/2000 | Stanley et al. |
| 6,245,360 B1 | 6/2001 | Markowitz |
| 6,254,898 B1 | 7/2001 | Bragaglia |
| 6,255,341 B1 | 7/2001 | DeMichele et al. |
| 6,258,384 B1 | 7/2001 | Stanley et al. |
| 6,291,533 B1 | 9/2001 | Fleischner |
| 6,326,034 B1 | 12/2001 | Mirsky et al. |
| 6,329,414 B1 | 12/2001 | Thomas et al. |
| 6,362,167 B1 | 3/2002 | Ghosal |
| 6,379,664 B1 | 4/2002 | Lou et al. |
| 6,426,076 B1 | 7/2002 | Pascoe |
| 6,426,362 B1 | 7/2002 | Miller et al. |
| 6,444,221 B1 | 9/2002 | Shapiro |
| 6,444,700 B1 | 9/2002 | DeMichele et al. |
| 6,451,341 B1 | 9/2002 | Slaga et al. |
| 6,495,177 B1 | 12/2002 | deVries et al. |
| 6,503,529 B1 | 1/2003 | Fleischner |
| 6,572,899 B1 | 6/2003 | Gorsek |
| 6,573,299 B1 | 6/2003 | Petrus |
| 6,579,544 B1 | 6/2003 | Rosenberg et al. |
| 6,584,980 B1 * | 7/2003 | Russo ............... A24B 15/301 131/275 |
| 6,602,512 B1 | 8/2003 | Cavazza |
| 6,632,459 B2 | 10/2003 | Graus et al. |

(Continued)

FOREIGN PATENT DOCUMENTS

WO    WO-2012088675 A1 *  7/2012  ............ A24B 15/30

OTHER PUBLICATIONS

Nordberg, Agneta, et al. "Chronic nicotine treatment reduces β-amyloidosis in the brain of a mouse model of Alzheimer's disease (APPsw)." Journal of neurochemistry 81.3 (2002): 655-658.*

(Continued)

*Primary Examiner* — Bethany P Barham
*Assistant Examiner* — Peter Anthopolos
(74) *Attorney, Agent, or Firm* — Dan DeLaRosa

(57) ABSTRACT

An antioxidant formulation for use with electronic cigarettes is provided and the formulation comprises: Vitamin A, Vitamin E, Trans-Resveratrol, polyphenol, and tertiary butyl hydroquinone.

20 Claims, No Drawings

(56) References Cited

U.S. PATENT DOCUMENTS

| | | |
|---|---|---|
| 6,646,013 B1 | 11/2003 | Barker et al. |
| 6,660,293 B2 | 12/2003 | Giordano et al. |
| 6,667,063 B2 | 12/2003 | Crum |
| 6,686,340 B2 | 2/2004 | Rath |
| 6,693,129 B2 | 2/2004 | Rath |
| 6,733,899 B2 | 5/2004 | Uehara et al. |
| 6,753,325 B2 | 6/2004 | Rosenbloom |
| 6,770,663 B2 | 8/2004 | Wagle et al. |
| 6,797,729 B1 | 9/2004 | Byrne et al. |
| 6,805,880 B1 | 10/2004 | Hojgaard et al. |
| 6,814,983 B2 | 11/2004 | Giordano et al. |
| 6,844,012 B1 | 1/2005 | Forceville et al. |
| 6,845,777 B2 | 1/2005 | Pera |
| 6,849,613 B2 | 2/2005 | Prasad et al. |
| 6,863,904 B2 | 3/2005 | Giordano et al. |
| 7,399,755 B2 | 7/2008 | Prasad et al. |
| 2002/0146463 A1 | 10/2002 | Clayton |
| 2002/0182196 A1 | 12/2002 | McCleary |
| 2002/0182585 A1 | 12/2002 | Kindness et al. |
| 2002/0193323 A1 | 12/2002 | Yegorova |
| 2003/0055012 A1 | 3/2003 | Carter |
| 2003/0103954 A1 | 6/2003 | Rosenbloom |
| 2003/0104080 A1 | 6/2003 | Singh et al. |
| 2003/0105027 A1 | 6/2003 | Rosenbloom |
| 2003/0108624 A1 | 6/2003 | Kosbab |
| 2003/0119909 A1 | 6/2003 | Stanislaus |
| 2003/0147981 A1 | 8/2003 | Gillam |
| 2003/0161863 A1 | 8/2003 | Ballevre et al. |
| 2003/0215430 A1 | 11/2003 | Petrus |
| 2004/0043013 A1 | 3/2004 | McCleary |
| 2004/0082536 A1 | 4/2004 | Cooper et al. |
| 2004/0106674 A1 | 6/2004 | Rich et al. |
| 2004/0109882 A1 | 6/2004 | Schonrock et al. |
| 2004/0223962 A1 | 11/2004 | Riordan |
| 2005/0009779 A1 | 1/2005 | Kiliaan et al. |
| 2005/0241658 A1* | 11/2005 | Pera .................. A23G 3/36 131/352 |
| 2010/0200008 A1* | 8/2010 | Taieb .................. A24F 47/008 131/360 |
| 2014/0150785 A1* | 6/2014 | Malik .................. A61M 15/06 128/202.21 |

OTHER PUBLICATIONS

Srivareerat, Marisa, et al. "Chronic nicotine restores normal Aβ levels and prevents short-term memory and E-LTP impairment in Aβ rat model of Alzheimer's disease." Neurobiology of aging 32.5 (2011): 834-844.*

Marambaud, Philippe, Haitian Zhao, and Peter Davies. "Resveratrol promotes clearance of Alzheimer's disease amyloid-β peptides." Journal of Biological Chemistry 280.45 (2005): 37377-37382.*

Trela, Brent C., and Andrew L. Waterhouse. "Resveratrol: isomeric molar absorptivities and stability." Journal of Agricultural and Food Chemistry 44.5 (1996): 1253-1257.*

Bieschke, Jan, et al. "EGCG remodels mature α-synuclein and amyloid-β fibrils and reduces cellular toxicity." Proceedings of the National Academy of Sciences 107.17 (2010): 7710-7715.*

Mandel, Silvia A., et al. "Cell signaling pathways and iron chelation in the neurorestorative activity of green tea polyphenols: special reference to epigallocatechin gallate (EGCG)." Journal of Alzheimer's disease 15.2 (2008): 211-222.*

Eftekharzadeh, Bahareh, Nader Maghsoudi, and Fariba Khodagholi. "Stabilization of transcription factor Nrf2 by tBHQ prevents oxidative stress-induced amyloid β formation in NT2N neurons." Biochimie 92.3 (2010): 245-253.*

Van Arnum, S. D. (2000). Vitamin A. In Kirk-Othmer Encyclopedia of Chemical Technology, (Ed.). doi: 10.1002/0471238961. 2209200101181421.a01.*

Casani, R. (2000). Vitamin E. In Kirk-Othmer Encyclopedia of Chemical Technology, (Ed.). doi: 10.1002/0471238961. 2209200103011901.a01.*

Shahidi, F. "Antioxidants in food and food antioxidants." Food/nahrung 44.3 (2000): 158-163.*

Shahidi, Fereidoon, and Ying Zhong. "Novel antioxidants in food quality preservation and health promotion." European Journal of Lipid Science and Technology 112.9 (2010): 930-940.*

* cited by examiner

MICRONUTRIENT FORMULATION IN ELECTRONIC CIGARETTES

RELATED APPLICATION

This application is related to U.S. Patent Provisional Application Ser. No. 62/070,395 filed on Aug. 25, 2014 entitled "Antioxidant Micronutrients in Electronic Cigarettes".

BACKGROUND OF THE INVENTION

Field of the Invention

This invention presents novel concepts relative to the use of unique antioxidant strategies to reduce the potential adverse effects of electronic cigarette (E-cig) use. The strategies include decreasing oxidative damage and inflammation, major factors in E-cig related adverse health effects, by employing agents that 1) directly scavenge excess free radicals by elevating dietary and endogenous antioxidant levels, and 2) indirectly reduce oxidative damage and inflammation by activating factors that increase antioxidant enzyme levels. The strategy also employs a novel mixture of agents that are incorporated directly into the E-cig liquid as well as an orally-consumed unique combination of antioxidant micronutrients.

SUMMARY OF THE INVENTION

In an embodiment, the present invention provides for an antioxidant formulation for supporting health in human beings comprising: Vitamin A, Vitamin E, Trans-Resveratrol, polyphenol, and tertiary butyl hydroquinone (TBHQ). In another embodiment, the present invention relates to an antioxidant formulation is to be used in a liquid form for electronic cigarettes. In yet another embodiment, the present invention provides for an antioxidant formulation is composed of lipid soluble components. In a further embodiment, the present invention relates to an antioxidant formulation is to be inhaled by human beings. In still another embodiment, the present invention provides for an antioxidant formulation wherein additional ingredients are chosen from a group comprising: Vitamin A, Vitamin E, Vitamin C, Calcium, Niacin, Vitamin D, Vitamin B, Folic Acid, Biotin, Pantothenic Acid, Co-enzyme Q10, N-acetyl cysteine, and Alpha Lipoic Acid. In still yet another embodiment, the present invention provides for an antioxidant formulation is to be supplemented with a secondary antioxidant formulation. In a futher embodiment, the present invention provides for a secondary antioxidant formulation comprises Vitamin A, Vitamin E, Natural mixed carotenoids, Vitamin C, Vitamin D, B-vitamins, Selenium, Co-enzyme Q10, Alpha-lipoic acid, N acetyl cysteine, L-carnitine, Omega-3-fatty acids, Resveratrol, Green tea polyphenol, Curcumin, Genistein, and Allicin. In another embodiment, the present invention provides for a secondary antioxidant formulation is to be taken orally. In still a further embodiment, the present invention relates to secondary antioxidant formulation is to be taken at least once a day. In another embodiment, the present invention provides for secondary antioxidant formulation of is to be taken twice a day.

In a further embodiment, the present invention relates to an electronic cigarette comprising an antioxidant formulation and the formulation comprises: Vitamin A, Vitamin E, Trans-Resveratrol, polyphenol, and tertiary butyl hydroquinone (TBHQ).

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The specific example below will enable the invention to be better understood. However, they are given merely by way of guidance and do not imply any limitation.

Because tobacco cigarette smoking caused adverse health effects and cessation was difficult due to nicotine addiction, efforts were made to develop a non-tobacco cigarette. In 1963, Dr. Herbert A. Gilbert patented a smokeless non-tobacco cigarette which drew moistened air through a heating element to generate vapor resembling tobacco cigarette smoke. In 2003, Hon Lik, a Chinese pharmacist, patented an Electronic-cigarette (E-cig) which was essentially a rechargeable lithium battery powered device that produced an aerosol vapor resembling tobacco cigarette smoke. The vapor is formed by heating a solution of propylene glycol and glycerin with or without nicotine at high temperatures (40-65° C.). Whether E-cigs have less long-term health consequences than tobacco cigarettes or aid in smoking cessation is unknown. Limited studies have been performed on the effects of vapor on human health but a comparative analysis of E-cig vapor and tobacco cigarette smoke showed that some common toxic chemical levels are lower in E-cigs. Some additional toxic chemicals that are found in the vapor of E-cigs that are not present in tobacco cigarette smoke, and vice versa.

It is proposed that increased oxidative stress and chronic inflammation produced by the constituents of the E-cig vapor are primary biochemical defects that may contribute to adverse health effects. Therefore, this invention describes the scientific rationale and evidence to suggest that addition of multiple micronutrients into the E-cig liquid may protect against injurious effects of toxic chemicals in the vapor. In addition, an oral supplement of micronutrients may provide overall protection against oxidative damage and chronic inflammation produced by the oxidizing agents, carcinogens and ultrathin particles of the heavy metals in the vapor.

E-cig Components:

An E-cig consists of a stainless steel shell, a rechargeable lithium ion battery, a small chamber containing miniaturized electronics and a tiny atomizer which vaporizes the E-cig liquid that may contain propylene glycol, glycerin, with or without varying amounts of nicotine and flavoring which include tobacco, menthol, mint, chocolate, coffee, apple, cherry, and caramel. The E-cig liquid fills the cartridge. The battery is connected to the vaporizer chamber which contains electronic control chips and an atomizer. The atomizer consists of a small heating element which vaporizes the E-cig liquid, as well as wicking materials that draw in the liquid. The atomizer and cartridge are also combined in a single unit called a cartomizer. Many E-cigs have a light-emitting diode on the end which lights up resembling actual flame when the users inhale. The user attaches a cartridge containing the E-cig liquid to the vaporizing chamber. The tip of the cartridge serves as the mouth piece and the user inhales the way they would inhale a tobacco cigarette. This inhalation process activates the atomizer to heat the E-cig liquid containing nicotine in the cartridge in order to produce vapor resembling tobacco cigarette smoke during exhalation. The nicotine vapor enters the lung and produces a nicotine "high".

Chemical Constituents of E-cig Vapor:

The levels of chemical constituents such as nicotine, toxic organic compounds and heavy metals in the E-cig vapor are highly variable (1-4). Although E-cigs deliver nicotine at a level of about 20% of that delivered by tobacco cigarettes, saliva levels of nicotine are similar in both sets of users (5, 6). The levels of toxic and carcinogenic compounds in E-cig vapor were 1-2 orders of magnitude lower than in the tobacco cigarette smoke, but higher than in nicotine inhalers (7). The E-cig vapor also contains propylene oxide (a product of heated propylene glycol), a potential carcinogen, acrolein (a product of heated glycerin) which can cause irritation in the upper respiratory tract and, in some products, detectable levels of tobacco-specific nitrosamines (8-10). Although the vapor of E-cigs may contain formaldehyde, acetaldehyde, isoprene, acetic acid,2-butanodione, acetone, propanol, propylene glycol and diacetin, the levels were lower than in tobacco cigarette smoke (11). A comparative analysis of potentially toxic and carcinogenic compounds, such as carbonyls, volatile organic compounds, nitrosamines and heavy metals in E-cig vapor showed levels that were many times lower than those in tobacco cigarette smoke (7).

Various E-cig components contain metals, such as copper wire coated with silver, tin, copper, aluminum, nickel, and silicate. E-cig vapor may contain particles of tin, silver, iron, copper, aluminum and silicate, and nanoparticles of tin, chromium and nickel (3). The concentrations of these metals in the E-cig vapor were often higher than those found in tobacco cigarette smoke. These particles can induce inflammation in tissues especially in the lung. Nanoparticles from the vapor can accumulate in various tissues including the lung, liver, kidney, heart and brain (12-15).

Effects on Human Health

The users of E-cigs develop nicotine addiction similar to that found in smokers of tobacco cigarettes. E-cig vapor with ultrathin particles of tin was very toxic to human pulmonary fibroblasts (3). Ultrathin particles of metals produced cytotoxic effects in vitro and in vivo (16, 17). Cobalt, chromium and chromium oxide nanoparticles can be toxic to mammalian cells in culture (18, 19), whereas nanoparticles of nickel hydroxide can induce oxidative stress and inflammation in the lung and heart of mice (20). Other adverse health effects of E-cigs include throat and mouth irritation, cough, nausea, and vomiting (4). In a mouse model, long term exposure to E-cig vapor increased infiltration of inflammatory cells including eosinophils into the airways, stimulated the production of cytokines interleukin-4 (IL-4), IL-5 and IL-13, and aggravated the asthmatic airway inflammation and airway hyper-responsiveness (21).

In clinical experience, a 20 year-old user of E-cigarettes developed acute eosinophilic pneumonia (22). In nine volunteer E-cig users, the levels of functional exhaled nitric oxide, a quantitative measure of airway inflammation, increased in the vapor. In addition, the levels of 1,2-propannediol, glycerin, nicotine, polycyclic aromatic hydrocarbons, carbonyls and ultrathin particulate matters of certain metals increased in the indoor air possibly inducing a "second-hand smoke" phenomenon (23). Because of the presence of high levels of nicotine, ultrathin particles of metals, oxidizing agents and volatile organic compounds in the E-cig vapor, the risk of cardiac arrhythmias and hypertension may increase and enhance the possibility of developing cardiovascular events (24). In addition, an increased risk of lung disease also exists in E-cig users. It has been suggested that E-cig use may constrict airways and aggravate the symptoms of asthma, emphysema or chronic bronchitis (25). Also, the levels of exhaled nitric oxide increased in users of E-cigarettes containing nicotine, but not in users of E-cigarettes without nicotine (23). Increased production of nitric oxide can lead to enhanced levels of peroxynitrite, a deadly form of free radical.

Reducing Health Effects of E-cigs by Decreasing Oxidative Stress and Inflammation:

Since E-cig vapor contains oxidizing agents such as propylene oxide, carcinogens such as nitrosamines, inflammatory agents such as acrolein, and ultrathin particles of heavy metals, it is likely that long-term E-cig may induce increased oxidative stress and chronic inflammation in various tissues, especially in the lung. Chronic inflammation releases pro-inflammatory cytokines, prostaglandins, adhesion molecules, complement proteins and free radicals all of which are toxic to cells. Ultraparticles of heavy metals would primarily accumulate in lung tissue and be a constant source of inflammation. Since these particles cannot be readily removed, it would be desirable to block their effects and/or protect tissues from the action of toxic chemicals released from inflammatory cells. Thus, reducing oxidative stress and chronic inflammation is one of the rational choices for reducing the potential health risks E-cigs in humans.

Optimally Reducing Oxidative Stress and Inflammation:

Elevation of the levels of antioxidant enzymes as well as dietary and endogenous antioxidant chemicals is essential for optimally reducing oxidative stress and chronic inflammation. Supplementation with antioxidant micronutrients can elevate their levels in the body. However, elevation of the levels of antioxidant enzymes is a complex process. The levels of antioxidant enzymes are elevated by activation of a transcriptional factor nuclear factor-erythroid 2-related factor-2 (Nrf2) which translocates itself from the cytoplasm to the nucleus where it binds with the antioxidant response element (ARE) to increase the transcription of genes coding for antioxidant enzymes. Activation of Nrf2 occurs by reactive oxygen species (ROS)-dependent and ROS-independent mechanisms. In addition, elevated levels of antioxidant enzymes are also dependent upon the binding ability of Nrf2 with ARE in the nucleus. The age-related decline in antioxidant enzymes in the liver of old rats compared to that in young rats was due to this reduction in the binding ability of Nrf2 with ARE. Treatment with alpha-lipoic acid restored this defect, increased the levels of antioxidant enzymes and restored the loss of glutathione in the liver of old rats (26).

ROS-dependent mechanism of Nrf2 activation: Normally, Nrf2 is associated a protein which acts as an inhibitor of Nrf2 (INrf2) in the cytoplasm (27). INrf2 acts as a sensor for ROS/electrophilic stress. In response to increased ROS, Nrf2 dissociates itself from INrf2 and translocates into the nucleus where it binds with ARE and up-regulates antioxidant genes.

ROS-independent mechanism of Nrf2 activation: Antioxidants such as vitamin E, the flavonoid, genistein (28), allicin, an organosulfur compound in garlic (29), sulforaphane, a organosulfur compound in cruciferous vegetables (30), kavalactones such as methysticin, kavain and yangonin (31) and dietary restriction (32) activate Nrf2 by ROS-independent mechanisms.

Nrf2 Response to ROS During Acute and Chronic Oxidative Stress:

Acute oxidative stress during strenuous exercise causes translocation of Nrf2 from the cytoplasm to the nucleus where it binds with ARE to up-regulate antioxidant genes. However, during chronic oxidative stress Nrf2 becomes unresponsive to ROS. Therefore, supplementation with selected non-toxic agents in combination may be useful in optimally reducing chronic oxidative stress because they can activate Nrf2 by ROS-independent mechanisms as well as elevate the levels of dietary and endogenous antioxidant micronutrients.
1. Agents that reduce oxidative stress by directly scavenging free radicals: These include dietary antioxidants, such as vitamin A, beta-carotene, vitamin C, and vitamin E, and endogenous antioxidants, such as glutathione, alpha-lipoic acid, and coenzyme Q10.
2. Agents that reduce oxidative stress by activating Nrf2 via an ROS-independent mechanism: These include vitamin E (28) and coenzyme Q10 (33).
3. Agents that reduce oxidative stress directly by scavenging free radicals as well as indirectly by activating Nrf2 via an ROS-independent mechanism: These include vitamin E (28), alpha-lipoic acid,(26), curcumin (34), resveratrol (35, 36), omega-3-fatty acids (37, 38) and N-acetyl cysteine (NAC) (39).

Reducing Chronic Inflammation:

Activation of Nrf2 suppresses inflammation. Antioxidants and other agents, individually and in combination, from the above groups have been shown to reduce chronic inflammation (40-47).

Example Antioxidant Formulation for E-Cig Liquid:

Primary Lipid Soluble Components

Per ml of liquid (approximately equivalent to smoking two packs of tobacco cigarettes):

|  | Target Dose: | Dosage Range: |
|---|---|---|
| Vitamin A (retinyl palmitate) | 2000 IU | 20-3000 IU |
| Vitamin E (d-alpha-tocopheryl acetate) | 25 IU | 0.5-50 IU |
| Vitamin E (d-alpha-tocopheryl succinate) | 25 IU | 0.5-50 IU |
| Trans-Resveratrol | 20 mg | 1-100 mg |
| Green tea polyphenol | 20 mg | 1-100 mg |
| Tertiary butyl hydroquinone (TBHQ) | 2 mg | 0.5-20 mg |

Doses in the above example are recommended but can be flexible. The synthetic antioxidant TBHQ is included in the E-cig liquid to prevent formation of oxidation products of propylene glycol and other constituents and, thereby, reduce the damaging effects of oxidized products on the lung. In addition, a synthetic antioxidant is necessary to prevent the degradation of vitamins A and E in order to increase the levels of antioxidants in the lung. The primary lipid soluble combination can optimally reduce oxidative stress and chronic inflammation in the lung indirectly by activating the Nrf2/ARE pathway by an ROS-independent mechanism, and directly by scavenging free radicals.

Example Formulation of Secondary Components:
Vitamin A 29.41 IU
Vitamin C 5.88 mg
Vitamin E (d-alpha tocopheryl acetate) 1.18 IU
Vitamin E (d-alpha tocopheryl succinate) 1.18 IU
Calcium 0.62 mg
Niacin 0.18 mg
Vitamin D3 2.35 IU
Vitamin B1 0.024 mg
Vitamin B2 0.03 mg
Vitamin B6 0.03 mg
Folic Acid 4.7 mcg
Vitamin B12 0.06 mcg
Biotin 1.18 mcg
Pantothenic Acid 0.06 mg
Co-enzyme Q10 0.22 mg
N-acetyl cysteine 1.47 mg
Alpha Lipoic Acid 0.22 mg Doses in the above example are recommended but can be flexible.

Temperature Stability:

A temperature range of 45-60° C. is needed to convert E-cig liquid into vapor. All polyphenols including resveratrol and green tea polyphenol are stable at a temperature 100° C. At 125° C., significant degradation of these polyphenols occurs (48). Degradation of vitamin E occurs at a temperature range of 180-260° C. for 20-80 minutes. This can be prevented by TBHQ (49). Vitamin A levels during sterilization of pre-pasteurized milk at 85° C. were maintained above 95% (50).

Supplemental Oral Micronutrients:

Oxidizing agents, carcinogens and ultraparticles of metals are present in E-cig vapor and not only accumulate in the lung, but also in the blood stream and are deposited in other organs including the brain. In order to protect the organ systems of the entire body, it is essential to supplement the antioxidants in the E-cig liquid with orally-consumed micronutrients.

Example Daily Formulation for E-cig Users
Vitamin A (retinyl palmitate)
Vitamin E (both d-alpha-tocopherol and d-alpha-tocopheryl succinate)
Natural mixed carotenoids,
Vitamin C (calcium ascorbate)
Vitamin D
B-vitamins,
Selenium
Co-enzyme Q10
Alpha-lipoic acid
N acetyl cysteine
L-carnitine
Omega-3-fatty acids
Resveratrol
Green tea polyphenol
Curcumin
Genistein
Allicin Doses in the above example are recommended but can be flexible. These agents can optimally reduce oxidative stress and chronic inflammation indirectly by activating the Nrf2/ARE pathway by an ROS-independent mechanism, and by directly scavenging free radicals. No iron, copper or manganese is included because these trace minerals are known to interact with vitamin C to produce free radicals. These trace minerals are absorbed from the intestinal tract more readily in the presence of antioxidants than in their absence and that could result in excess body stores of these minerals. Increased iron stores have been linked to increased risk of several chronic diseases (51).

The supplement combination should be taken orally and divided into two doses, half in the morning and the other half in the evening with a meal. This is because the biological half-lives of micronutrients are highly variable which can create excessive fluctuations in the tissue levels of these micronutrients. Even only a two-fold difference in the levels of certain micronutrients such as alpha-tocopheryl succinate can cause a marked difference in the expression of gene profiles (Prasad, KN, unpublished data). The twice-daily dosing will help maintain relatively consistent levels of micronutrients in the body.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. An e-cigarette cartridge containing an atomizable liquid composition comprising Vitamin A, Vitamin E, trans-resveratrol, a green tea polyphenol, and tert-butylhydroquinone, wherein the atomizable liquid composition is nicotine free.

2. The e-cigarette cartridge of claim 1, wherein the Vitamin A is retinyl palmitate.

3. The e-cigarette cartridge of claim 2, wherein the amount of retinyl palmitate in the atomizable liquid composition is from 20 IU to 3,000 IU.

4. The e-cigarette cartridge of claim 1, wherein the Vitamin E is d-alpha-tocopheryl acetate.

5. The e-cigarette cartridge of claim 4, wherein the amount of d-alpha-tocopheryl acetate in the atomizable liquid composition is from 0.5 IU to 50 IU.

6. The e-cigarette cartridge of claim 1, wherein the Vitamin E is d-alpha-tocopheryl succinate.

7. The e-cigarette cartridge of claim 6, wherein the amount of d-alpha-tocopheryl succinate in the atomizable liquid composition is from 0.5 IU to 50 IU.

8. The e-cigarette cartridge of claim 1, wherein the Vitamin E is a mixture of d-alpha-tocopheryl acetate and d-alpha-tocopheryl succinate.

9. The e-cigarette cartridge of claim 1, wherein the amount of trans-resveratrol in the atomizable liquid composition is from 1 mg to 100 mg.

10. The e-cigarette cartridge of claim 1, wherein the amount of green tea polyphenol in the atomizable liquid composition is from 1 mg to 100 mg.

11. The e-cigarette cartridge of claim 1, wherein the amount of tert-butylhydroquinone in the atomizable liquid composition is from 0.5 mg to 20 mg.

12. An e-cigarette cartridge containing an atomizable liquid composition comprising:
    retinyl palmitate;
    d-alpha-tocopheryl acetate;
    d-alpha-tocopheryl succinate;
    trans-resveratrol;
    a green tea polyphenol; and
    tert-butylhydroquinone; and
    wherein the atomizable liquid composition is nicotine free.

13. The e-cigarette cartridge of claim 12, wherein the amount of retinyl palmitate in the atomizable liquid composition is from 20 IU to 3,000 IU.

14. The e-cigarette cartridge of claim 12, wherein the amount of d-alpha-tocopheryl acetate in the atomizable liquid composition is from 0.5 IU to 50 IU.

15. The e-cigarette cartridge of claim 12, wherein the amount of d-alpha-tocopheryl succinate in the atomizable liquid composition is from 0.5 IU to 50 IU.

16. The e-cigarette cartridge of claim 12, wherein the amount of trans-resveratrol in the atomizable liquid composition is from 1 mg to 100 mg.

17. The e-cigarette cartridge of claim 12, wherein the amount of green tea polyphenol in the atomizable liquid composition is from 1 mg to 100 mg.

18. The e-cigarette cartridge of claim 12, wherein the amount of tert-butylhydroquinone in the atomizable liquid composition is from 0.5 mg to 20 mg.

19. An e-cigarette cartridge containing an atomizable liquid composition comprising:
    retinyl palmitate, wherein the amount of retinyl palmitate in the atomizable liquid composition is from 20 IU to 3,000 IU;
    d-alpha-tocopheryl acetate, wherein the amount of d-alpha-tocopheryl acetate in the atomizable liquid composition is from 0.5 IU to 50 IU;
    d-alpha-tocopheryl succinate, wherein the amount of d-alpha-tocopheryl succinate in the atomizable liquid composition is from 0.5 IU to 50 IU;
    trans-resveratrol, wherein the amount of trans-resveratrol in the atomizable liquid composition is from 1 mg to 100 mg;
    a green tea polyphenol; and
    tert-butylhydroquinone, wherein the amount of tert-butylhydroquinone in the atomizable liquid composition is from 0.5 mg to 20 mg; and
    wherein the atomizable liquid composition is nicotine free.

20. The e-cigarette cartridge of claim 19, wherein the amount of green tea polyphenol in the atomizable liquid composition is from 1 mg to 100 mg.

* * * * *